(12) United States Patent
Grant et al.

(10) Patent No.: US 6,764,391 B1
(45) Date of Patent: Jul. 20, 2004

(54) PNEUMATIC DEVICE

(75) Inventors: Sidney Grant, London (GB); Roger Lawrence Beale, Middlesex (GB); Raghuvir Ishwarbhai Patel, Essex (GB); Frederick James Garod Bowler, Essex (GB)

(73) Assignee: Medivance Instruments Limited (GB)

( * ) Notice: Subject to any disclaimer, the term of this patent is extended or adjusted under 35 U.S.C. 154(b) by 53 days.

(21) Appl. No.: 10/129,992

(22) PCT Filed: Nov. 13, 2000

(86) PCT No.: PCT/GB00/04335
§ 371 (c)(1),
(2), (4) Date: Aug. 19, 2002

(87) PCT Pub. No.: WO01/36159
PCT Pub. Date: May 25, 2001

(30) Foreign Application Priority Data

Nov. 15, 1999 (GB) ............................................. 9926980

(51) Int. Cl.[7] .................................................. A61C 3/02
(52) U.S. Cl. .............................. 451/99; 433/88; 451/90
(58) Field of Search ............................ 451/90, 99, 91, 451/75, 38, 60, 102; 433/88, 80; 222/161; 239/144, 311; 285/156

(56) References Cited

U.S. PATENT DOCUMENTS

| 3,270,463 A | | 9/1966 | Ashworth | |
|---|---|---|---|---|
| 3,517,461 A | * | 6/1970 | Baldwin et al. | 451/99 |
| 4,232,487 A | * | 11/1980 | Brown | 451/88 |
| 5,199,229 A | | 4/1993 | Herold et al. | |
| 5,618,177 A | * | 4/1997 | Abbott | 433/88 |
| 5,626,472 A | * | 5/1997 | Pennetta | 433/80 |
| 5,934,904 A | | 8/1999 | Elrod et al. | |
| 5,941,702 A | * | 8/1999 | Sharp et al. | 433/88 |
| 6,106,288 A | * | 8/2000 | Brassil et al. | 433/88 |
| 6,129,547 A | * | 10/2000 | Cise et al. | 433/80 |
| 6,132,212 A | * | 10/2000 | Horiguchi et al. | 433/88 |
| 6,390,816 B2 | * | 5/2002 | Ito et al. | 433/88 |

FOREIGN PATENT DOCUMENTS

| DE | 15 77 564 | 1/1970 |
|---|---|---|
| DE | 25 49 804 | 5/1977 |
| FR | 2 572 925 | 5/1986 |

* cited by examiner

Primary Examiner—Joseph J Hail, III
Assistant Examiner—Anthony Ojini
(74) Attorney, Agent, or Firm—Caesar, Rivise, Bernstein, Cohen & Pokotilow, Ltd.

(57) ABSTRACT

A powder, such as an abrasive powder, is delivered from a pressure vessel having an outlet in the floor communicating with a flow of pressurized gas. A container of the particulate material is located within the pressure vessel and has an outlet to dispense small portions of the particulate material. The material in the container is at substantially the same pressure as that in the pressure vessel itself.

9 Claims, 3 Drawing Sheets

PNEUMATIC DEVICE

BACKGROUND OF THE INVENTION

The invention relates to a pneumatic device arranged to deliver a particulate material. One illustrative example of the device is to pneumatically deliver abrasive or polishing dental powder material. More particularly but not exclusively the invention is useful in so-called micro-airabrasion e.g. in dentistry.

It is one object of the invention to provide a device for this purpose which is clean and reliable and easy to maintain.

BRIEF SUMMARY OF THE INVENTION

According to the invention in one aspect there is provided apparatus for pneumatically delivering particulate material, the apparatus comprising a pressure vessel having an outlet in the floor communicating with a flow of pressurised gas; a container for the particulate material to be delivered, the container being located in the vessel above the floor and having an outlet located to supply a small amount of particulate material to the outlet in the vessel floor; the container being arranged so that the material in the container is at substantially the same pressure as in the remainder of the vessel; and means for supplying pressurised gas in the vessel whereby the material is delivered via the vessel outlet at substantially uniform pressure.

Preferably the container is mounted within the vessel so that it may be surrounded by pressurised gas and the particulate material in the container is at substantially uniform gas pressure throughout its height. Most preferably the container is replaceable, and provided as an accessory. This can be sealed to avoid the risk of contamination before installation in the vessel.

Preferably at least the upper part of the container has translucent or transparent walls. When the container is mounted in a pressure vessel which protrudes above a housing the operator, e.g. a dentist, can easily see the level of material in the container.

Preferably the vessel is vibrated by a motor. Preferably the apparatus includes at least one switch arranged to energise or de-energise the motor in synchronism with the supply of pressurised gas.

Preferably the access to the interior of the vessel is via a top cap which has a pressure resistant seal, for example by a bayonet fitting arrangement.

In another aspect the invention provides a method of delivering particulate material pneumatically, the method comprising locating a container of the particulate material in a pressure vessel having an outlet in the floor, the outlet communicating with a flow of pressurised gas, the container having an outlet arranged to deliver a small amount of the particulate material to the vessel outlet; and supplying pressurised gas into the vessel to entrain particulate material from the container and substantially maintain pressurised gas in the vessel and one the particulate material in the container, whereby the material is delivered via the vessel outlet at substantially uniform pressure.

In another aspect, the invention provides a container for use in apparatus as defined, the container housing the particulate material, and having an exit port in the floor above a platform which together define an open sided chamber, the chamber being releasably sealed by a stopper, the top of the container also having a releasable seal.

BRIEF DESCRIPTION OF SEVERAL VIEWS OF THE DRAWINGS

In order that the invention may be well understood it will not be described by way of example only with reference to the accompanying diagrammatic drawings, in which.

DETAILED DESCRIPTION OF THE INVENTION

Figure 1:
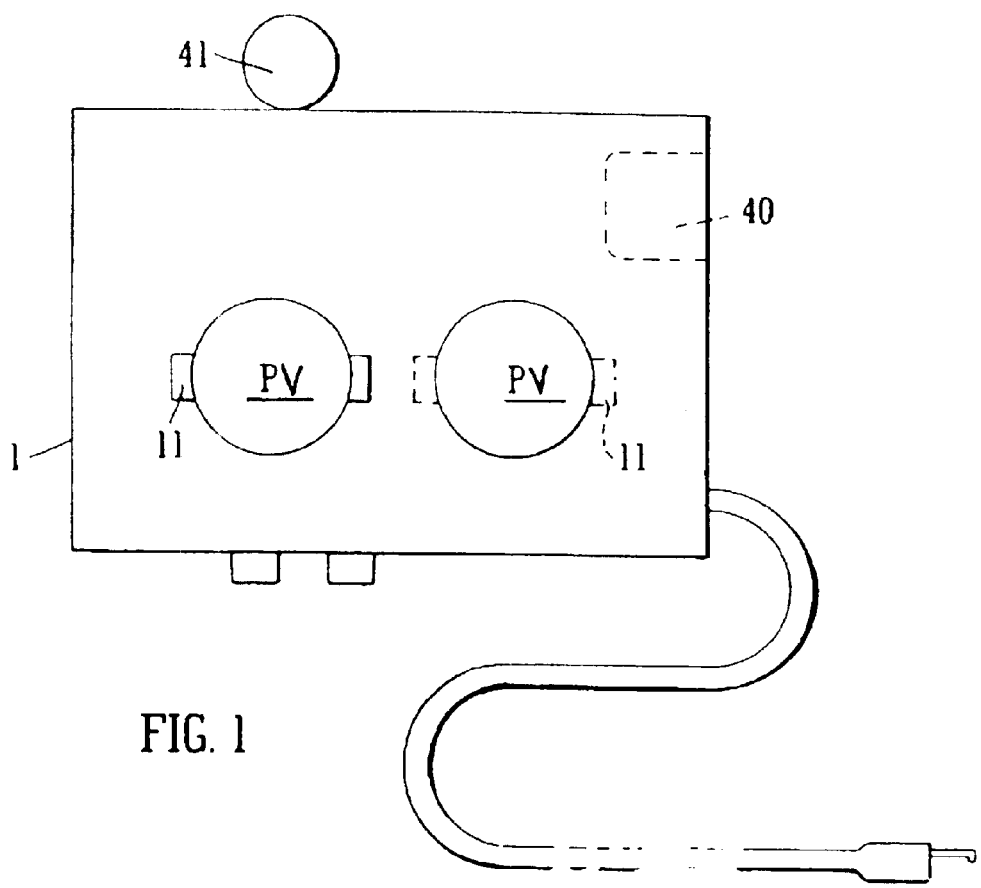
FIG. 1 is a plan view of one apparatus, partly in section.
Figure 2:
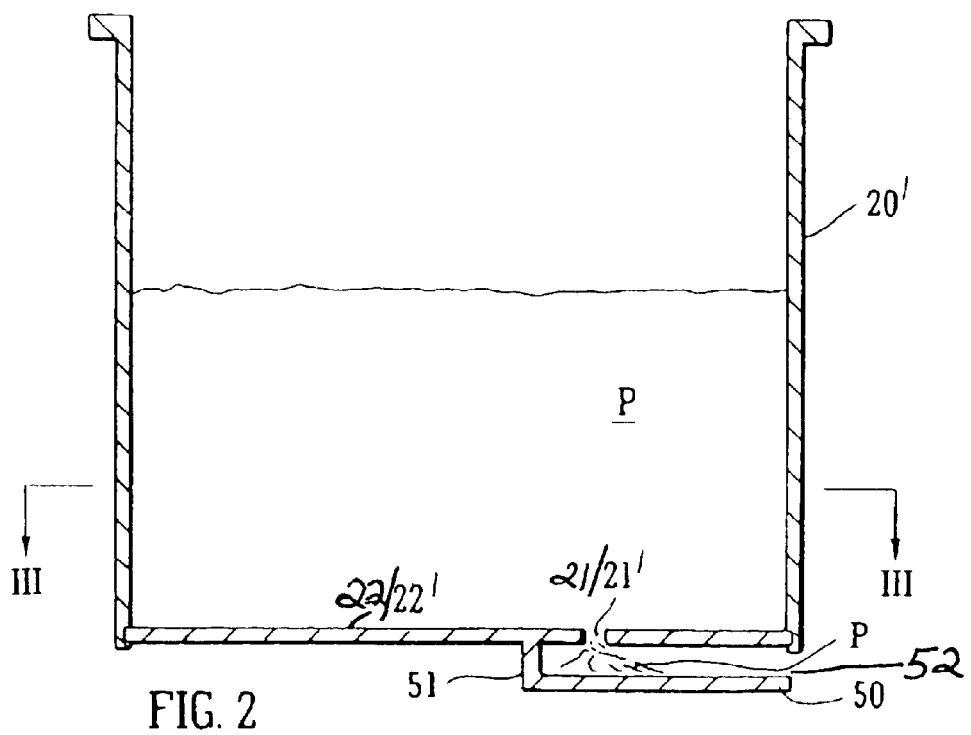
FIG. 2 is an elevation partly in section of one pressure vessel having a container.
Figure 3:
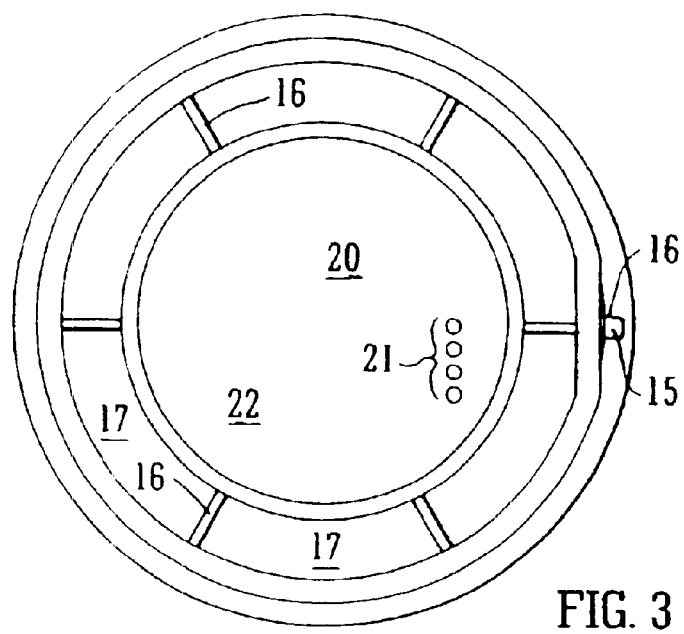
FIG. 3 is a transverse view of the vessel of FIG. 2 taken on lines III—III.
Figure 4:
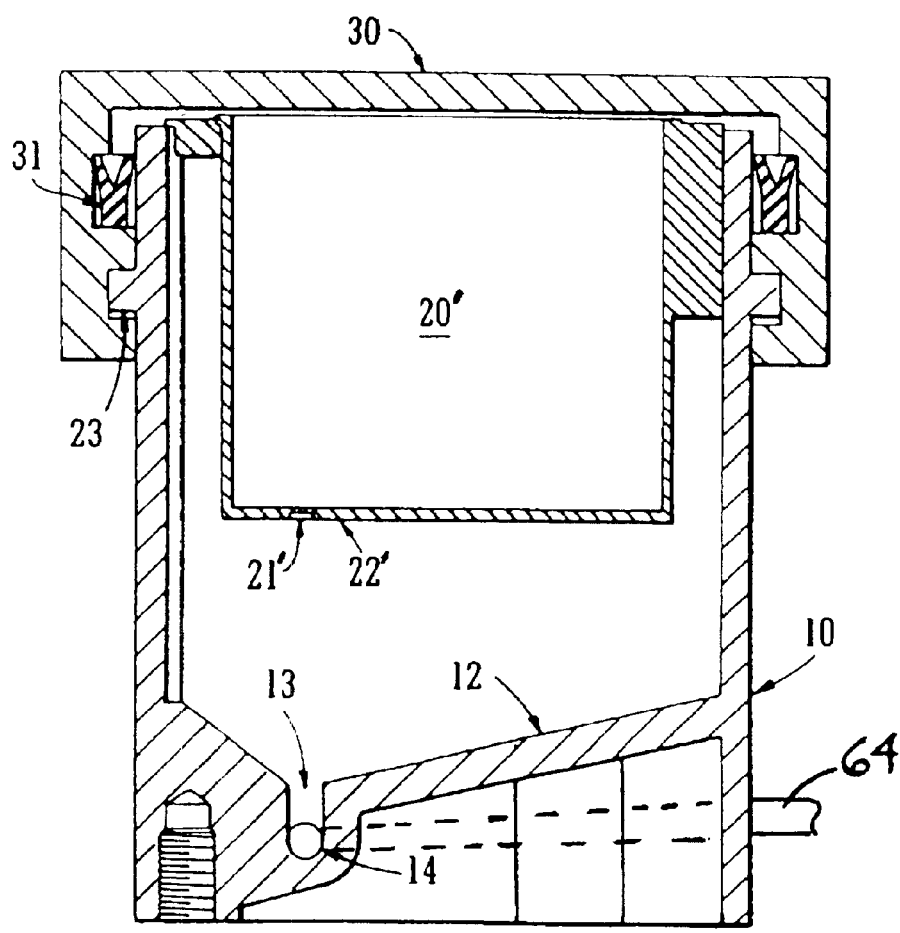
FIG. 4 is a vertical section through the pressure vessel and showing another container.

The containers of FIGS. 2 and 4 are the same except for the floor and ports therein, so that the same reference numerals are used to describe the same parts in the different embodiments with the addition of a prime to represent the different floor and ports.

Figure 5:
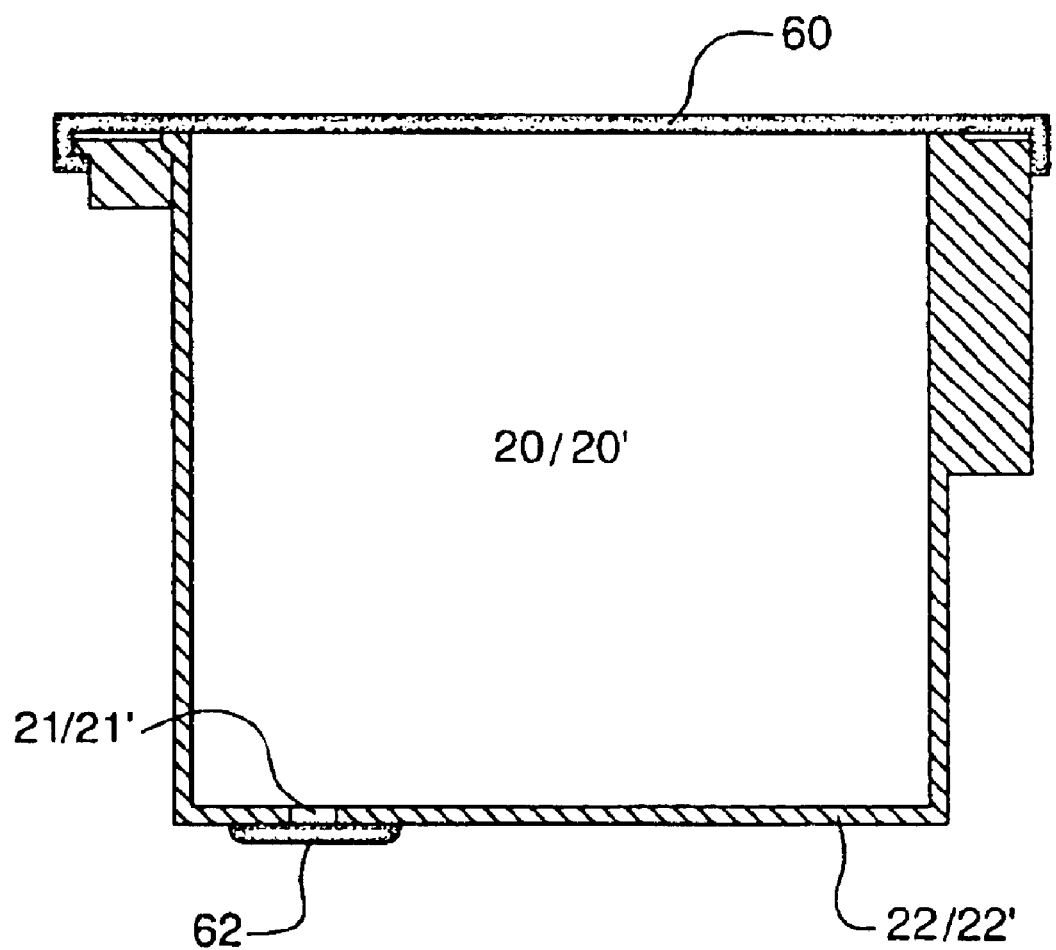
FIG. 5 is a vertical section through either container showing a lid thereon.

The apparatus shown in FIGS. 1–4 comprises a housing 1 containing two pressure vessel assembly PV (the number may be varied). Each assembly comprises a generally cylindrical pressure vessel or receptacle 10 mounted above a motor 11, e.g. a linear pneumatic vibrator, arranged to vibrate the vessel. The vessel wall is made of a translucent or transparent plastics. The vessel has a sloping floor 12 leading to the mouth 13 of a channel 14 extending chordally of the vessel and open at its ends. The channel is in communication with a pipeline 64 carrying a pressurised gas, e.g., air. The inner wall surface at the top of the vessel has recesses 15 arranged to receive arms or wings 16 at the outer top of a container or cartridge 20. (There is a flat at one side for polarisation purposes.) The arms 16 define an annular gap 17 about the container 20. The container holds the particulate material to be dispensed e.g. aluminium oxide or sodium bicarbonate powder for dental use. The container has a row of small exit ports 21 in its flat floor 22, the ports being vertically above the mouth 13 of the channel 14. The container is supplied with a tear off lid 60 shown in FIG. 5, and in that condition the outside of the floor at exit ports 21 is taped over by tape 62 to seal the holes. This lid and tape are both removed just before installation in the vessel.)

The outside wall surface at the top of the vessel 10 has shoulders 23 to be engaged in bayonet fitting manner with those inside a cap 30 having a pressure sealing rubber or plastics washer 31.

When the cap 30 is fitted on the vessel 10 the entire volume is contained and maybe supplied with pressurised gas, e.g. air in a leak-proof manner via the pipeline 64 leading to the channel 14. Such air can circulate about the container 20 and reach the material at the top of the container by passing through the gap 17.

Air supply lines lead from an external supply to both pressure vessels and then to a valve block 40 containing three pinch valves. One line leads to an exhaust container 41; the others lead to the handpiece. The compressed air is separated on entry, one branch is factory set to 7 bar max going to the infinitely variable air pressure control and the infinitely variable vibrator control is factory set to say 4 bar, and supplies all the control circuitry.

An output line leads to a dental tool, having a tungsten tip and an aperture through which the material is delivered.

In use, the dentist visually checks the level of material in the containers 20 through the transparent wall. He selects which material he wants, he then presses a switch, e.g. a foot-pedal, which opens the respective valve in the valve block 40. The motor 11 is energised to vibrate the respective pressure vessel 10. Pressured air flows through the channel 14 entraining particulate material from the container 20 and via the line to the tool tip where it is used e.g. to microabrade damaged areas of the tooth, e.g. decay along the side of a fissure. The abrasion not only removes defective substance, but leaves a keying surface for a subsequently applied adhesive filling composition. When the dentist switches off, the air supply stops and the motor is de-energised but pressured air remains in the vessel. Excess material is passed to the exhaust vessel 40.

Because the pressurised air is always present in the entire volume of the vessel and on the particulate material in the container, there is no surge of pressure. As a result there always is a uniform delivery of pressurised material; the particulate material is not spread about to cause a mess; there is little wastage. Because a sealed container is supplied there is little risk of contamination.

In the embodiment of FIG. 4 the container or cartridge 20' is similar to the container or cartridge 20, except that it has a single exit port 21' in the floor 22' above a lower ledge or platform 50 (not shown in FIG. 4). The underside of the floor 22' and the platform 50, and the vertical wall 51 define a chamber which however is open to one side 52 (see FIG. 2). The volume of the chamber can be varied by the height of the wall 51 and the area of the platform 50. The power P descends through the single exit port 21' to fall on to the platform 50 and then form a pile of loose particles. When the pressurised air is supplied it is simple to urge the powder to drop down to the main outlet of the vessel.

There is no risk of the powder in the container 20' being so compacted as to block the port 21'. The air pressure may be low, say about 7 bar, which is lower than the usual level. The powder may be vibrated under low force, e.g. a linear pneumatic vibrator.

The container will usually be shipped full of the particulate material with a plate-like stopper, not shown, filling the open chamber to prevent premature escape of the powder. This is removed just before installation in the main vessel. The top of the container is also covered by a releasable seal.

The apparatus enables the user to easily switch between types of cutting media in the different vessels. The system is totally pneumatic and can either work directly from an existing air supply, an independent compressor or from bottled gas, provided that the air pressure is within a specified input say of 5 to 8 bar. This initiates the vibrators which start coincidentally with the output of air into the hand piece. Once the foot pedal is released, the air is instantly cut off and any residual air/powder mix is allowed to escape into a dust collecting exhaust vessel 41 situated at the rear of the unit. The output from the receptacles is controlled by the pinch valves which allow the abrasive powder to pass through without detriment to the pneumatic control devices. The general layout is such that servicing is simple and the parts are accessible. The housing can be easily be wiped cleaned with cleaners as recommended in the maintenance section of this manual.

The replaceable tips are made from high quality stainless tubing with tungsten carbide nozzles with a choice of 0.4 mm, 0.6 mm and 0.8 mm diameter orifice.

To set up the device a high pressure hose, not shown, which is both flexible but non kinking, 4 mm outside diameter of a suitable length is connected from the air supply to a push-in connector (not shown) at the back of the housing 1 and a foot control switch is connected to the two inlet compression fittings situated at the back of the housing. The air should not be switched on until the following have been attended to: (1) The foot pedal sited in a convenient position. (2) The vessels are located in their recommended positions (fine in the left and medium in the right). (3) Both the caps secured. (4) The correct diameter nozzle screwed into the hand piece. (5) Protective eye wear is placed on the patient, the operator and the assistant(s). (6) Aspirators switched on and ready to use (intra oral and external). (7) Protective cape placed over the patients clothes.

When replacing the powder containers, ensure that the sealing strip at the bottom is completely removed before peeling off the top seal. Carefully lower the powder receptacle into the vessels guided by arms 16 ensuring that it is fully seated. Replace the caps, apply light downward pressure, turn in a clockwise direction until positive resistance is felt. Turn on the air at the front of the housing. This will cause a hissing sound as the two vessels are charged with pressurised air. Select the material to use by turning the switch either to"FINE" or"MEDIUM" (which refers to the vessels). Set the air pressure and mixture controls. Select and fit nozzle to the hand piece. The device is now ready for use as soon as the foot switch is depressed.

It is advantageous to switch the device off when not in use. Apart from preventing accidental switching on by treading on the foot switch, it also preserves the integrity of the pinch valves. The exhaust vessel 40 collects all the residual particles left in the system. This should be emptied at the end of every surgery.

The device is very versatile, as illustrated by the following:

Cleaning: Switch to "FINE" (sodium bicarbonate) air pressure 6 bar mixture 1.5 bar, nozzle +0.6–0.8 mm.

Scaling: Switch to"MEDIUM" (50μm aluminium oxide) air pressure 4 bar, mixture 1.5 bar, nozzle +0.6–0.8 mm. finish as with "Clean" setting.

Fissure sealant: Switch to "MEDIUM" (50 μm aluminium oxide) air pressure 6 bar, mixture 1.5 bar, nozzle +0.4–0.6 mm.

Cavity Prep.: Switch to "MEDIUM" (50 μm aluminium oxide) air pressure 6 bar, mixture 2 bar, nozzle +0.4–0.6 mm (depending on size of pre.)

Root planning: Switch to "MEDIUM" (50 μm aluminium oxide) air pressure 6 bar, mixture 1.5 bar, nozzle +0.6/0.8 mm. finish as with "Clean" setting.

Orthodontics: Switch to "MEDIUM" (50 μm aluminium oxide) air pressure 4 bar, mixture 1.5 bar, nozzle +0.8 mm.

What is claimed is:

1. Apparatus for pneumatically delivering particulate material to a dental tool, the apparatus comprising:
    (a) a pressure vessel having a hollow interior, a floor and an outlet in the floor communicating with a flow of pressurized gas;
    (b) a receptacle container containing the particulate material to be delivered, the container being located in the vessel at a distance above the floor and having a container outlet located above the vessel outlet and in communication therewith via the hollow interior of the pressure vessel, the container outlet being dimensioned to supply a small amount of the particulate material to exit therefrom to the vessel outlet;
    (c) means for supplying pressurised gas into the vessel and for circulating the pressurized gas about the container so that the material in the container is at substantially the same pressure as in the remainder of the vessel; and
    (d) power means to vibrate the vessel to cause the small amount of particulate material to exit from the container outlet for free fall through the hollow interior of the pressure vessel to the pressure vessel outlet and be pneumatically transported via a pipeline at substantially uniform pressure to the dental tool.

2. Apparatus according to claim 1, wherein the container is removably sealed by a releasable seal to provide a transportable container containing particulate material.

3. Apparatus according to claim 1, wherein the access to the interior of the vessel is via a top cap which has a pressure resistant seal.

4. Apparatus according to claim 3, wherein the cap is engaged with the top of the vessel by a bayonet fitting arrangement.

5. Apparatus according to claim 1, wherein at least a portion of the vessel has translucent or transparent walls.

6. Apparatus according to claim 1, including a pressure receptacle to receive any particulate material in the pipeline left when the supply of gas is switched off.

7. Apparatus according to claim 1, wherein the container is open sided and has a platform below a single exit port which is arranged to that the particulate material will descend from the vessel outlet on to the platform.

8. A container for use in apparatus according to claim 1, the container containing dental particulate material, and having an exit port in the floor above a platform which together define an open sided chamber, the exit port being releasably sealed by a stopper, the top of the container also having a releasable seal.

9. A method of delivering particulate material pneumatically to a dental tool, the method comprising:

(a) providing a container containing the particulate material in a pressure vessel having a hollow interior, a floor and an outlet in the floor, the outlet communicating with a flow of pressurised gas leading to the dental tool;

(b) locating the container above the vessel outlet and in communication with the vessel outlet via the hollow interior of the pressure vessel, the container having a container outlet located above the vessel outlet and dimensioned to a small amount of the particulate material to the vessel outlet;

(c) supplying pressurised gas into the vessel to entrain particulate material from descending from the outlet of the container; and (d) providing and actuating power means to vibrate the vessel to cause particulate material to exit from the outlet of the container for free fall through the hollow interior of the vessel to the outlet of the vessel whereby the material is delivered pneumatically at substantially uniform pressure to the dental tool.

* * * * *